United States Patent [19]

Sato et al.

[11] Patent Number: 5,874,617

[45] Date of Patent: Feb. 23, 1999

[54] PROCESS OF PRODUCING ANILIDE COMPOUND

[75] Inventors: Shinichi Sato, Annaka; Noriyuki Koike, Takasaki, both of Japan

[73] Assignee: Shin-Etsu Chemical Co., Ltd., Tokyo, Japan

[21] Appl. No.: 8,302

[22] Filed: Jan. 16, 1998

[30] Foreign Application Priority Data

Jan. 16, 1997 [JP] Japan ..................................... 9-017900

[51] Int. Cl.⁶ ................................................... C07C 209/02

[52] U.S. Cl. ............................ 564/202; 556/419; 564/158

[58] Field of Search ..................................... 564/202, 158; 556/419

*Primary Examiner*—Brian M. Burn
*Attorney, Agent, or Firm*—Oblon, Spivak, McClelland, Maier & Neustadt, P.C.

[57] ABSTRACT

A process of producing an anilide compound, including reacting an acid fluoride with an N-silylaniline compound in the presence of a basic compound, is provided. According to the process, a desired anilide compound can be produced in a high yield without requiring a filtering step.

12 Claims, No Drawings

PROCESS OF PRODUCING ANILIDE COMPOUND

BACKGROUND OF THE INVENTION

1. Field of the Invention

The present invention relates to a process of producing an anilide compound.

2. Description of the Prior Art

To produce an anilide compound, conventionally, a method is known wherein an acid fluoride and an aniline compound are reacted. However, in this reaction, since hydrogen fluoride is produced concomitantly, for a reason of safety, it is required to catch the hydrogen fluoride using an acid scavenger, such as a tertiary amine and a basic nitrogen-containing compound. In addition, the use of a tertiary amine produces an amine hydrofluoride in the form of a solid and a step is required to filter off this salt, which is a defect.

On the other hand, the reaction of an acid fluoride with an N-silylaniline compound proceeds hardly or even if they are reacted, the yield is very low.

SUMMARY OF THE INVENTION

Therefore, an object of the present invention is to provide a process of producing efficiently an anilide compound with the above problems being solved and without requiring a filtering step.

The inventors of the present invention have investigated intensively to attain the above object and have found that the above object can be attained by the following process.

The present invention provides a process of producing an anilide compound, comprising reacting an acid fluoride with an N-silylaniline compound in the presence of a basic compound.

According to the process of the present invention, an anilide compound can be synthesized in a high yield. This process does not require a step of filtering an amine hydrogen fluoride in the form of a solid, which step is required in conventional processes. That is, since the by-product involved in the present process is a highly volatile silyl fluoride, the by-product can be easily removed, for example, by vacuum distillation.

DETAILED DESCRIPTION OF THE PREFERRED EMBODIMENTS

The present invention is described in detail below.

Acid Fluoride

The acid fluoride used in the present invention includes, for example, compounds represented by the general formulas (1) to (2):

$$R^1\text{—CO—F} \quad (1)$$

wherein $R^1$ denotes a substituted or unsubstituted monovalent organic group, and $$F\text{—CO—}R^2\text{—CO—F} \quad (2)$$

wherein $R^2$ denotes a substituted or unsubstituted bivalent organic group.

In the general formula (1), the substituted or unsubstituted monovalent organic group denoted by $R^1$ includes, for example, an alkyl group generally having 1 to 1,000 carbon atoms and preferably 1 to 500 carbon atoms, such as a methyl group, an ethyl group, and a propyl group; a cycloalkyl group generally having 3 to 20 carbon atoms and preferably 3 to 12 carbon atoms, such as a cyclopentyl group and a cyclohexyl group; an alkenyl group generally having 2 to 20 carbon atoms and preferably 2 to 12 carbon atoms, such as a vinyl group and an ally group; an aryl group generally having 6 to 30 carbon atoms and preferably 6 to 18 carbon atoms, such as a phenyl group, a tolyl group, and a xylyl group; an aralkyl group generally having 7 to 30 carbon atoms and preferably 7 to 19 carbon atoms, such as a benzyl group and a phenylethyl group; corresponding monovalent substituted groups in which part or all of the hydrogen atoms of the above monovalent groups have been replaced, for example, with a halogen atom(s), such as chlorine, fluorine, and bromine, and/or a cyano group(s) (e.g., a chloromethyl group, a chlorophenyl group, a perfluoroalkyl, a dibromophenyl group, or a cyanoethyl group); and monovalent groups in the form of an oligomer or polymer (e.g., monovalent perfluoropolyether groups, polyether groups, polyester groups, polyimide groups and polyamide groups).

In the general formula (2), the substituted or unsubstituted bivalent organic group denoted by $R^2$ includes, for example, an alkylene group generally having 1 to 1000 and preferably 1 to 500 carbon atoms, such as a methylene group, an ethylene group, a propylene group, and a trimethylene group; a cycloalkylene group generally having 3 to 20 and preferably 3 to 12 carbon atoms, such as a cyclopentylene group and a cyclohexylene group; an alkenylene group generally having 2 to 20 carbon atoms and preferably 2 to 12 carbon atoms; an arylene group generally having 6 to 30 carbon atoms and preferably 6 to 18 carbon atoms, such as a phenylene group, a tolylene group, a xylylene group, and a naphthylene group; corresponding bivalent substituted groups in which part or all of the hydrogen atoms of the above bivalent groups have been replaced, for example, with a halogen atom(s), such as chlorine, fluorine, and bromine, and/or a cyano group(s) (e.g., a chloromethylene group, a chlorophenylene group, and a perfluoroalkylene group); and bivalent groups in the form of an oligomer or polymer (e.g., bivalent perfluoropolyether groups, polyether groups, polyester groups, polyimide groups and polyamide groups).

Hereinbelow, specific examples of the acid fluoride are shown, wherein "a methyl group" is abbreviated to "Me" and "a phenyl group" is abbreviated to "Ph."

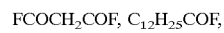

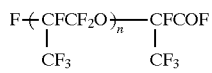

wherein n is an integer of 0 to 300,

wherein n is an integer of 0 to 300,

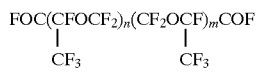

wherein m and n are independently each an integer of 0 to 200, provided that m and n are not simultaneously 0 and the average value of m+n ranges from 0 to 300, and

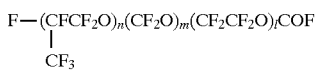

wherein l, m, and n are independently each an integer of 0 to 100 and the average value of l+m+n ranges 0 to 50.

N-silylaniline Compound

In the present process, it is essential to use an N-silylaniline compound as an aniline compound. The N-silylaniline compound includes, for example, a compound represented by the general formula (3):

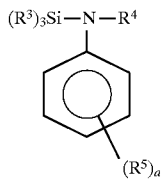

wherein a is an integer generally of 0 to 5 and preferably 0 to 2, $R^3$, which are the same or different, each denote an alkyl group generally having 1 to 10 carbon atoms and preferably 1 to 8 carbon atoms; an alkenyl group generally having 2–8 carbon atoms and preferably 2–6 carbon atoms, such as a vinyl group and an ally group; or an aryl group generally having 6–10 carbon atoms and preferably 6–8 carbon atoms, such as a phenyl group and a tolyl group, $R^4$ denotes a hydrogen atom, an alkyl group generally having 1 to 10 carbon atoms and preferably 1 to 8 carbon atoms, or a group denoted by the formula: —Si($R^3$)$_3$ in which $R^3$ has the same meaning as defined above, $R^5$ denotes a halogen atom, a nitro group, or a group denoted by the formula: —Si($R^3$)$_3$ in which $R^3$ has the same meaning as defined above, and if a is 2 or more, $R^5$ are the same or different.

The group represented by $R^3$ is preferably a methyl group because in that case the volatility of the silyl fluoride that is by-produced in the reaction in the present process, i.e., a compound denoted by the following formula:

wherein $R^3$ has the same meaning as defined above, becomes high.

Examples of the N-silylaniline compound denoted by the general formula (3) are shown below:

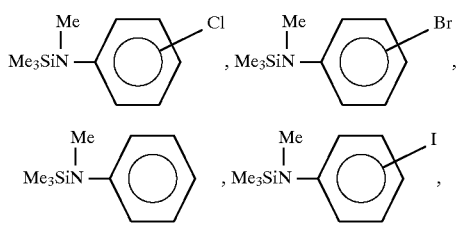

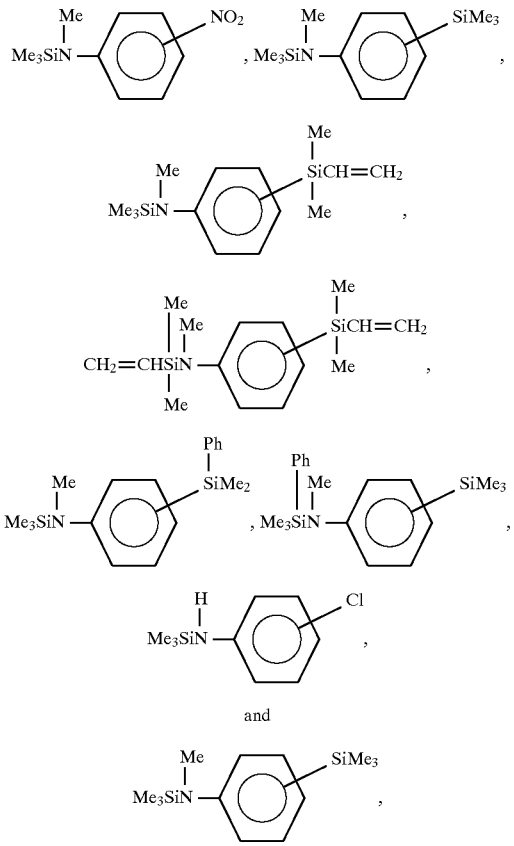

In the present process, the amount of the N-silylaniline compound is such that the N-silyl group in the N-silylaniline compound is present in an amount of generally 1.0 to 1.5 mol and preferably 1.0 to 1.2 mol per mol of the acid fluoride group (i.e., the —COF group).

Basic Compound

In the present process, by using a basic compound as a catalyst, the anilide compound can be obtained in a higher yield.

The basic compound includes, for example, a tertiary amine, such as triethylamine and tributylamine; and a basic nitrogen-containing compound, such as 1,5-diazabicyclo [5.4.0]-7-undecene (DBU), pentamethylguanidine, and pyridine. Among them, a tertiary amine is preferable and triethylamine is particularly preferable because in that case the yield of the obtained anilide compound is better.

The amount of the basic compound may be a so-called catalytic amount.

In the present process, use of a solvent is not particularly required but optionally a fluorine-containing solvent, such as m-xylene hexafluoride, p-xylene fluoride, and benzotrifluoride, may be used.

Further, reaction temperature may be 0° to 100° C. and particularly preferably 20° to 60° C. in view of reaction rate and because in that case the reaction temperature is higher than the boiling point of the tertiary amine which may be used as a catalyst. Reaction time is determined appropriately on the basis of the production scale and may be generally 1 to 10 hours.

Reaction

The present process is carried out in accordance with the following reaction:

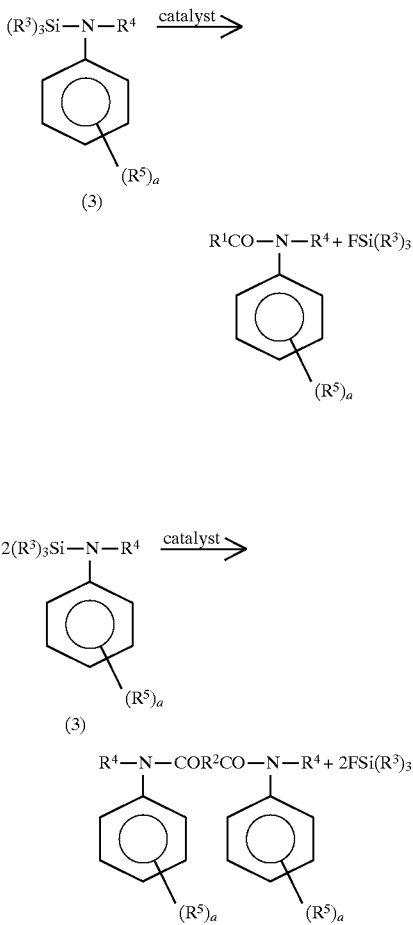

wherein $R^1$, $R^2$, $R^3$, $R^4$, $R^5$, and a have the same meanings as defined above.

In the present process, it is used that the bond energy between the silicon atom of the N-silylaniline compound and the fluorine atom of the acid fluoride group is large.

After the reaction, the silyl fluoride, the catalyst, and the solvent that has been optionally added are removed easily by purification means, generally, such as vacuum distillation.

The present process is useful as a means of introducing a phenylamide group to the end of the molecular chain of a polymer, particularly, a polymer having perfluoroalkylene groups, bivalent perfluoropolyether groups, or the like (i.e. cases in the above general formula (1), $R^1$ is a polymer chain and cases in the general formula (2), $R^2$ is a polymer). The obtained compound is useful as an intermediate for the production of fluororubbers, fluorogels, fluorine-containing adhesives, and the like.

EXAMPLES

The present invention will now be described specifically by reference to Examples.

Example 1

10.0 g of an acid fluoride represented by the following formula:

$$F\text{-}(CFCF_2O)_2\text{-}CFCOF,$$
$$\quad\quad\quad\; |\quad\quad\quad\quad |$$
$$\quad\quad\quad CF_3\quad\quad\quad CF_3$$

20.0 g of m-xylene hexafluoride, and 5.2 g (1.21 mol per mol of the acid fluoride group) of N-trimethylsilyl-N-methylmetachloroaniline were charged in a 50-ml four-necked flask equipped with an agitating rod, a thermometer, a Dimroth, and a dropping funnel and were stirred at 23° C. for 1 hour. The reaction proceeded hardly, which was confirmed by gas chromatography. Then, when 0.5 g of triethylamine was added to the mixture, heat was generated until the temperature reached 39° C. 1 hour after the addition, the reaction conversion was 99.4%, which was confirmed by gas chromatography. The reaction mixture was subjected to vacuum distillation to obtain 10.8 g (yield: 86.8%) of a fraction having a boiling point of 95° to 97° C./3 mmHg and a refractive index of 1.4864 (25° C.). This fraction was subjected to $^1$H-NMR, IR, and elementary analysis. The results are shown below.

$^1$H-NMR
δ 3.29 (s, N—CH$_3$, 3H)
δ 6.7–7.6 (m, arom., 4H)
IR
$v_{C=O}$ 1,700 cm$^1$
Elementary analysis

|  | C | F | O | N | Cl |
|---|---|---|---|---|---|
| Found | 31.01% | 52.12% | 7.75% | 2.26% | 5.72% |
| Calculated | 30.99% | 52.18% | 7.78% | 2.29% | 5.80% |

From the above results, it was confirmed that the obtained compound is a compound represented by the following formula:

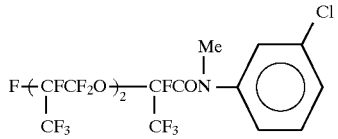

Example 2

50.0 g of an acid fluoride represented by the following formula:

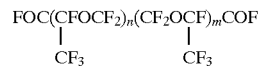

wherein m and n are independently each an integer of 1 to 30 and the average value of m+n is 35, 5.2 g (1.2 mol per mol of the acid fluoride group) of N-trimethylsilyl-N-methyl-m-(vinyldimethylsilyl)aniline, and 0.5 g of triethylamine were charged into a 100-ml four-necked flask equipped with an agitating rod, a Dimroth, and a dropping funnel and were stirred at 50° C. for 4 hours. After it was confirmed by gas chromatography that the peak intensity of the N-trimethylsilyl-N-methyl-m-(vinyldimethylsilyl) aniline was reduced to about 20% of the initial value, the reaction mixture was subjected to vacuum distillation to remove volatile components to obtain a viscous liquid in an amount of 49.6 g (yield: 94%).

This viscous liquid had a viscosity of 1785 cSt (25° C.), a specific gravity of 1.807 (25° C.), and a refractive index of 1.3238 (25° C.). The results of $^1$H-NMR, IR, and elementary analysis confirmed that the liquid was a compound represented by the following formula:

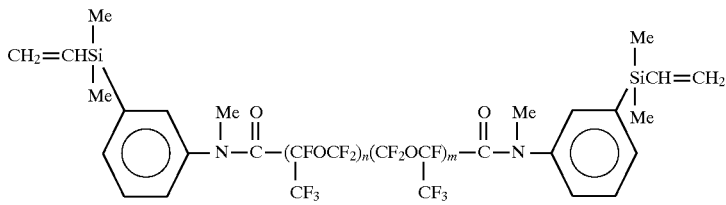

wherein m and n are independently each an integer of 1 to 30 and the average value of m+n is 35. The results of $^1$H-NMR, IR, and elementary analysis are shown below.

$^1$H-NMR
δ 0.36 (s, Si—CH$_3$, 12H)
δ 3.35 (s, N—CH$_3$, 6H)
δ 5.7–6.4 (m, Si—CH=CH$_2$, 6H)
δ 7.1–7.6 (m, arom., 8H)
IR
$υ_{C=O}$ 1,700 cm$^1$
Elementary analysis

| | Elementary analysis | | | | |
|---|---|---|---|---|---|
| | C | F | O | N | Si |
| Found | 24.78% | 64.24% | 9.18% | 0.43% | 0.87% |
| Calculated | 24.65% | 64.33% | 9.14% | 0.45% | 0.88% |

Example 3

1,000 g of an acid fluoride represented by the following formula:

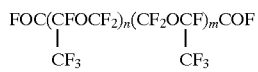

wherein m and n are independently each an integer of 1 to 30 and the average value of m+n is 35, 96.4 g (1.2 mol per mol of the acid fluoride group) of N-vinyldiemthylsilyl-N-methyl-m-(vinyldimethylsilyl)aniline, and 10.0 g of triethylamine were charged into a 2-litter four-necked flask equipped with an agitating rod, a Dimroth, and a dropping funnel and were stirred at 25° C. for 3 hours. After it was confirmed by gas chromatography that the peak intensity of the N-vinyldiemthylsilyl-N-methyl-m-(vinyldimethylsilyl) aniline was reduced to about 20% of the initial value, the reaction mixture was subjected to vacuum distillation to remove volatile components to obtain a viscous liquid in an amount of 956 g (yield: 94%).

This viscous liquid had a viscosity of 1849 cSt (25° C.), a specific gravity of 1.804 (25° C.), and a refractive index of 1.3249 (25° C.). The results of $^1$H-NMR, IR, and elementary analysis confirmed that the liquid was a compound represented by the following formula:

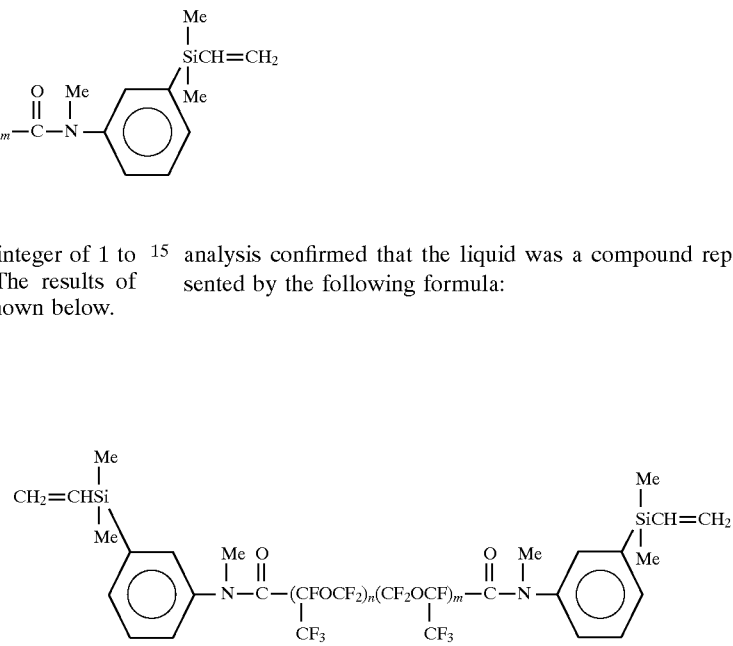

wherein m and n are independently each an integer of 1 to 30 and the average value of m+n is 35. The results of $^1$H-NMR, IR, and elementary analysis are shown below.

$^1$H-NMR
δ 0.37 (s, Si—CH$_3$, 6H)
δ 3.34 (s, N—CH$_3$, 3H)
δ 5.7–6.4 (m, Si—CH=CH$_2$, 3H)
δ 7.1–7.6 (m, arom., 4H)
IR
$υ_{C=O}$ 1,700 cm$^1$
Elementary analysis

| | Elementary analysis | | | | |
|---|---|---|---|---|---|
| | C | F | O | N | Si |
| Found | 24.69% | 64.35% | 9.22% | 0.43% | 0.86% |
| Calculated | 24.65% | 64.33% | 9.14% | 0.45% | 0.88% |

What is claimed is:

1. A process of producing an anilide compound, comprising reacting an acid fluoride with an N-silylaniline compound in the presence of a basic compound.

2. The process of producing an anilide compound of claim 1, wherein said basic compound is a tertiary amine.

3. The process of claim 1, wherein said acid fluoride is a compound represented by the general formula (1):

wherein R$^1$ denotes a substituted or unsubstituted monovalent organic group.

4. The process of claim 3, wherein the substituted or unsubstituted monovalent organic group denoted by R$^1$ is a group selected from the group consisting of an alkyl group having 1 to 1,000 carbon atoms; a cycloalkyl group having 3 to 20 carbon atoms; an alkenyl group having 2 to 20 carbon atoms; an aryl group having 6 to 30 carbon atoms; an aralkyl group having 7 to 30 carbon atoms; corresponding monovalent substituted groups in which part or all of the hydrogen atoms of the above monovalent groups have been replaced with a halogen atom(s) or a cyano group(s); and monovalent groups in the form of an oligomer or polymer.

5. The process of claim 1, wherein said acid fluoride is a compound represented by the general formula (2):

$$F-CO-R^2-CO-F \qquad (2)$$

wherein $R^2$ denotes a substituted or unsubstituted bivalent organic group.

6. The process of claim 5, wherein the substituted or unsubstituted bivalent organic group denoted by $R^2$ is a group selected from the group consisting of a substituted or unsubstituted alkylene group having 1 to 1,000 carbon atoms; a substituted or unsubstituted cycloalkylene group having 3 to 20; a substituted or unsubstituted alkenylene group having 2 to 20 carbon atoms; a substituted or unsubstituted arylene group having 6 to 30 carbon atoms; and bivalent groups in the form of an oligomer or polymer.

7. The process of claim 1, wherein said acid fluoride is selected from the group consisting of

$CF_3COF$, $C_7F_{15}COF$, $CH_3COF$, $PhCOF$, $CH_2=CHCOF$, $FCOCH_2COF$,

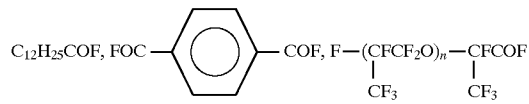

$C_{12}H_{25}COF$, FOC—⟨phenyl⟩—COF, $F-(CFCF_2O)_n-CFCOF$ with $CF_3$ groups wherein n is an integer of 0 to 300,

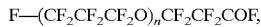

$F-(CF_2CF_2CF_2O)_nCF_2CF_2COF$, wherein n is an integer of 0 to 300,

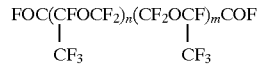

$FOC(CFOCF_2)_n(CF_2OCF)_mCOF$ with $CF_3$ groups wherein m and n are independently an integer of 0 to 200, provided that m and n are not simultaneously 0 and the average value of m+n ranges from 0 to 300, and

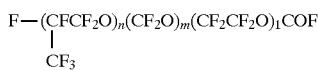

$F-(CFCF_2O)_n(CF_2O)_m(CF_2CF_2O)_lCOF$ with $CF_3$ wherein l, m, and n are independently an integer of 0 to 100 and the average value of l+m+n ranges 0 to 50.

8. The process of claim 1, wherein said N-silylaniline compound is a compound represented by the general formula (3):

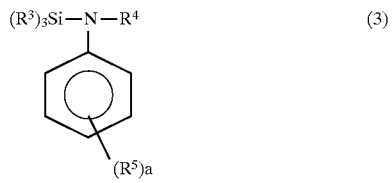

$(R^3)_3Si-N-R^4$ on phenyl with $(R^5)_a$ (3)

wherein a is an integer of 0 to 5, $R^3$, which are the same or different, and each denote an alkyl group having 1 to 10 carbon atoms; an alkenyl group having 2 to 8 carbon atoms; or an aryl group having 6 to 10 carbon atoms, $R^4$ denotes a hydrogen atom, an alkyl group having 1 to 10 carbon atoms, or a group denoted by the formula: $-Si(R^3)_3$ in which $R^3$ has the same meaning as defined above, $R^5$ denotes a halogen atom, a nitro group, or a group denoted by the formula: $-Si(R^3)_3$ in which $R^3$ has the same meaning as defined above, and if a is 2 or more, $R^5$ are the same or different.

9. The process of claim 8, wherein the compound represented by the above general formula (3) is selected from the group consisting of

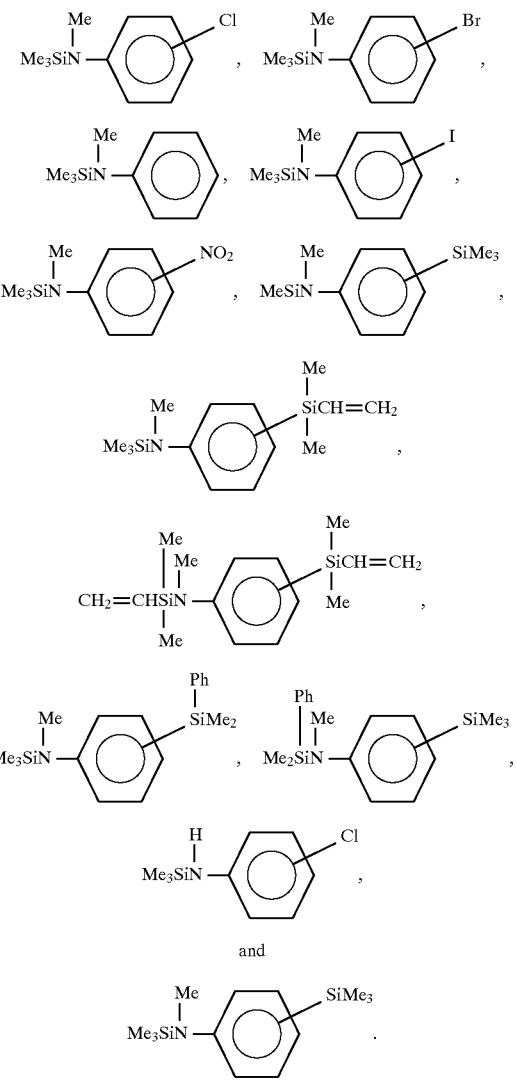

and

10. The process of claim 1, wherein said basic compound is selected from the group consisting of tertiary amines, such as triethylamine and tributylamine, 1,5-diazabicyclo[5.4.0]-7-undecene (DBU), pentamethylguanidine, and pyridine.

11. The process of claim 10, wherein said basic compound is triethylamine.

12. The process of claim 1, wherein the amount of the N-silylaniline compound is such that the N-silyl group of the N-silylaniline compound is present in an amount of 1.0 to 1.5 mol and preferably 1.0 to 1.2 mol per mol of the —COF group possessed by the acid fluoride compound.

* * * * *